United States Patent [19]

Kitamori et al.

[11] Patent Number: 4,808,828
[45] Date of Patent: Feb. 28, 1989

[54] METHOD OF AND APPARATUS FOR SIMULTANEOUS DETERMINATION

[75] Inventors: Takehiko Kitamori; Haruo Fujimori, both of Hitachi; Kazumichi Suzuki, Mito, all of Japan

[73] Assignee: Hitachi, Ltd., Tokyo, Japan

[21] Appl. No.: 937,050

[22] Filed: Dec. 2, 1986

[30] Foreign Application Priority Data

Dec. 2, 1985 [JP] Japan ................ 60-269269

[51] Int. Cl.$^4$ ............................................. G01N 21/64
[52] U.S. Cl. ............................. 250/458.1; 250/459.1;
356/73; 356/432
[58] Field of Search ................. 356/432 T, 73;
250/459.1, 458.1

[56] References Cited

U.S. PATENT DOCUMENTS 4,303,343 12/1981 Patel et al. .................... 356/432 T
4,413,504 11/1983 Voigtman et al. .............. 250/432 R

FOREIGN PATENT DOCUMENTS 37910 3/1980 Japan ..................... 356/432 T

OTHER PUBLICATIONS

Oda et al., "Determination of Ultra Trace Cadmium by Laser-Induced Photoacoustic Absorption Spectrometry", Anal. Chem. 50(7), Jun. 1978, pp. 865–867.
Oda et al., "Analysis of Turbid Solutions by Laser-Induced Photoacoustic Spectroscopy", Anal. Chem., 52, 1980, pp. 650–653.
Kitamori et al., "Determination of Sub-Part-Per-Trillion Amounts of Cobalt by Extraction and Photoacoustic Spectroscopy", Anal. Chem., 58, 1986, pp. 2275–2278.
W. S. Lyon (editor), *Analytical Spectroscopy*, "On-Line Uranium Determination Using Remote Fiber Fluorimetry", pp. 25–30, Elseveir Science Pub. B.V., Amsterdam, Netherlands.

*Primary Examiner*—Carolyn E. Fields
*Attorney, Agent, or Firm*—Antonelli, Terry & Wands

[57] ABSTRACT

A method of and an apparatus for simultaneous determination of constituents are disclosed in which a solution containing trace constituents is irradiated with an intensity-modulated electromagnetic wave having a predetermined wavelength, a photoacoustic signal and radiation from the electromagnetic-wave irradiation trace constituents are detected together with the emission spectrum thereof. The concentrations of the trace constituents are calculated from the magnitude of the photoacoustic signal, the intensity of the radiation, and calibration curves each formed for known concentrations of one of the trace constituents, and the trace constituents are identified by the above emission spectrum.

14 Claims, 5 Drawing Sheets

METHOD OF AND APPARATUS FOR SIMULTANEOUS DETERMINATION

BACKGROUND OF THE INVENTION

The present invention relates to a method of and an apparatus for qualitatively and quantitatively analyzing a plurality of trace constituents which are contained in a solution in the form of fine particles or ions, and more particularly to an analytical method and an analyzer suitable for qualitatively and quantitatively analyzing a plurality of trace constituents which are contained in a solution and include a trace constituent low in generation efficiency of photoacoustic signal.

The photoacoustic analysis and the fluorometric analysis have been used to determine a trace constituent contained in a solution. In each of them, a solution containing a trace constituent is irradiated with light (namely, an electromagnetic wave). Further, a photoacoustic signal generated by the light-irradiated trace constituent is detected in the photoacoustic analysis, and luminescence from the light-irradiated trace constituent is detected in the fluorometric analysis. The photoacoustic analysis is described, for example, on pages 865 to 867 of the June 1978 issue (Vol. 50, No. 7) of the "Analytical Chemistry", on pages 650 to 653 of the April 1980 issue (Vol. 52, No. 4) of the same, and on pages 2275 to 2278 of the November 1986 issue (Vol. 58, No. 11) of the same. Further, the fluorometric analysis is described, for example, in an article entitled "ON-LINE URANIUM DETERMINATION USING REMOTE FIBER FLUORIMETRY" by R. A. Malstrom and T. Hirschfeld ("Analytical Spectrometry", pages 25 to 30). In these publications, however, the use of only either one of the photoacoustic analysis or the fluorometric analysis is described.

A molecule or atom can be excited from a ground state to an excited state by the absorption of light. In many cases, the excited molecule or atom is deexcited to the ground state through a non-radiative or radiative relaxation process. At this time, excess energy is released, as the thermal energy, in the non-radiative relaxation process, and is released, as the optical energy, in the radiative relaxation process. A medium containing the above molecule or atom thermally expands on the basis of the thermal energy generated by the non-radiative relaxation, and thus an acoustic wave, that is, a photoacoustic signal is generated. While, fluorescence and phosphorescence are generated by the radiative relaxation process. When the quantum yield of non-radiative relaxation and the quantum yield of radiative relaxation are expressed by $\eta_1$ and $\eta_2$, respectively, the following formula is valid:

$$ti\ \eta_1 + \eta_2 \simeq 1 \tag{1}$$

That is, the photoacoustic effect and the fluorescence (or phosphorescence) generated by a substance which has absorbed light, are complementary to each other. Accordingly, a substance which can be detected at high sensitivity by the photoacoustic analysis, has low sensitivity to the fluorometric analysis. While, a substance which can be detected at high sensitivity by the fluorometric analysis, has low sensitivity to the photoacoustic analysis. However, as indicated by the formula (1), the photoacoustic signal and the fluorescence (or phosphorescence) are simultaneously generated by a substance to be determined, and a ratio of one of the photoacoustic signal magnitude and the fluorescence intensity to the other intensity depends upon the to-be-determined substance. Accordingly, almost all substances can be determined by measuring both the photoacoustic signal and the fluorescence (or phosphorescence). However, a limited number of substances can generate fluorescence or phosphorescence. Accordingly, the fluorometric analysis is applicable to only the above substances. Further, in a case where a first substance incapable of generating fluorescence (or phosphorescence) and a second substance generating strong fluorescence (or phosphorescence) and an extremely weak photoacoustic signal coexist in a medium, it is very difficult to determine each of the first and second substances accurately by only one of the photoacoustic analysis and the fluorometric analysis.

For example, in a case where a chemical species exhibits a plurality of valences, and the luminous efficiency of the chemical species varies with the valence thereof, it is impossible to determine both the concentration of the chemical species and the relative abundances of the above valences by one of the photoacoustic analysis and the fluorometric analysis. In a uranium extraction process in the reprocessing of nuclear fuel, sexivalent uranium U(VI) is extracted from tri-n-butyl phosphate dodecane solution. It is essential for quality control and safeguards that the abundance ratio between sexivalent uranium U(VI) and quadrivalent uranium U(IV) is measured. However, the sexivalent uranium U(VI) exhibits the fluorescence, but the quadrivalent uranium U(IV) does not fluoresce. Accordingly, it is impossible to analyze a solution containing U(VI) and U(IV) by conventional analytical methods.

SUMMARY OF THE INVENTION

An object of the present invention is to provide a method of and an apparatus for analyzing a plurality of trace constituents of a solution quantitatively and qualitatively, in which a photoacoustic signal and fluorescence (or phosphorescence) generated by the constituents are simultaneously measured to quantitatively determine each constituent with high accuracy and to identify the constituents.

In an analytical method according to the present invention, a solution containing trace constituents is irradiated with an intensity-modulated electromagnetic wave (for example, a light pulse), a photoacoustic signal generated by and radiation from the trace constituents are simultaneously detected, the constituent concentration is calculated from the intensities of the photoacoustic signal and the radiation, and each constituent is identified by the spectrum of the radiation.

According to the above analytical method, in a case where a solution contains a luminous constituent and a non-luminous constituent, the resultant concentration of these constituents can be determined by the photoacoustic signal, and the concentration of the luminous constituent can be determined by the radiation therefrom such as fluorescence or phosphorescence. Thus, the concentration of the non-luminous constituent is given by the difference between the resultant concentration of the constituents and the concentration of the luminous constituent. Further, according to the above analytical method, the photoacoustic analysis and the fluorometric analysis are carried out at the same time, and hence an analytical time is greatly shortened. Additionally, according to the above analytical method, a single sample solution is subjected to the photoacoustic analysis and the fluorometric analysis, and hence the amount of sample solution used is less, as compared with a case where an apparatus for photoacoustic analysis and an apparatus for fluorometric analysis are used independently of each other.

DESCRIPTION OF THE PREFERRED EMBODIMENTS

Embodiments of the present invention will be explained below, by reference to FIGS. 1 to 6.

Figure 1:
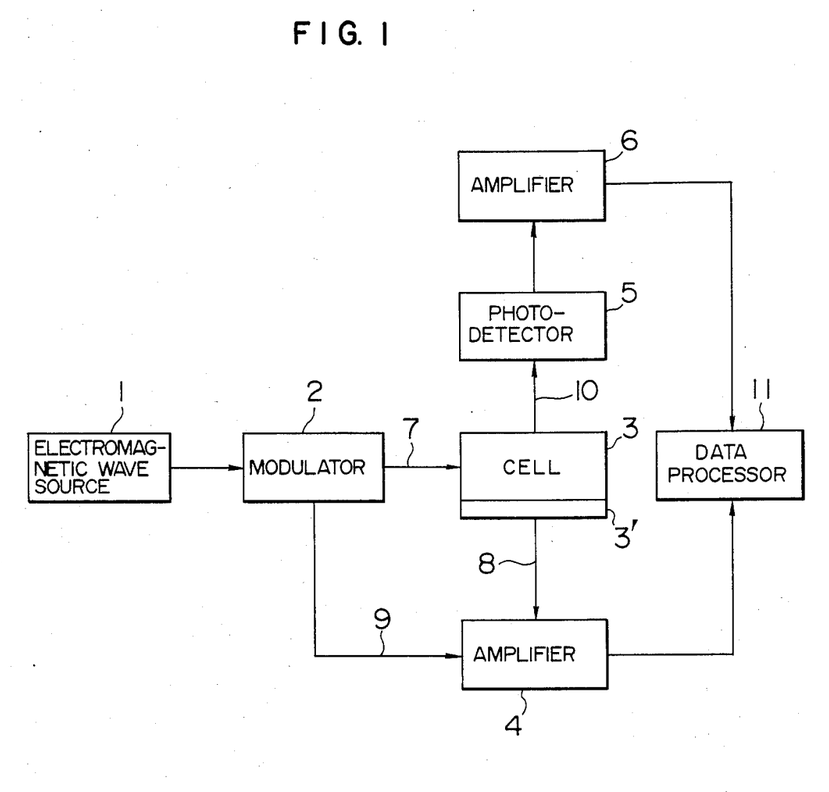
FIG. 1 is a block diagram showing the fundamental construction of an analyzer according to the present invention.

FIG. 1 shows the fundamental construction of an analyzer according to the present invention. Referring to FIG. 1, an electromagnetic wave emitted from an electromagnetic wave source 1 is converted by a modulator 2 into a periodically intensity-modulated wave, to be used as an excitation beam 7 for generating a photoacoustic signal and fluorescence (or phosphorescence). While, a solution containing trace constituents to be determined is introduced into a cell 3. The solution may be held within the cell 3, or may continuously pass through the cell 3. When the excitation beam 7 travels into the cell 3, the trace constituents contained in the solution generate a photoacoustic signal and fluorescence (or phosphorescence). The photoacoustic signal is detected by an acoustic wave detector 3' mounted on the cell 3, to be converted into an electric signal 8. Since the electric signal 8 is very weak, an amplifier 4 amplifies the signal 8 in synchronism with a modulating signal 9 from the modulator 2, thereby discriminating a photoacoustic signal component from background noise.

Meanwhile, light 10 radiated from the constituents such as fluorescence or phosphorescence is converted by a photodetector 5 into an electric signal, which is amplified by an amplifier 6. Data based upon the photoacoustic signal and data based upon the fluorescence (or phosphorescence) are processed by a data processor 11, to determine the constituent concentration of the solution, to identify each constituent, and to display such results of the processing.

Figure 2:
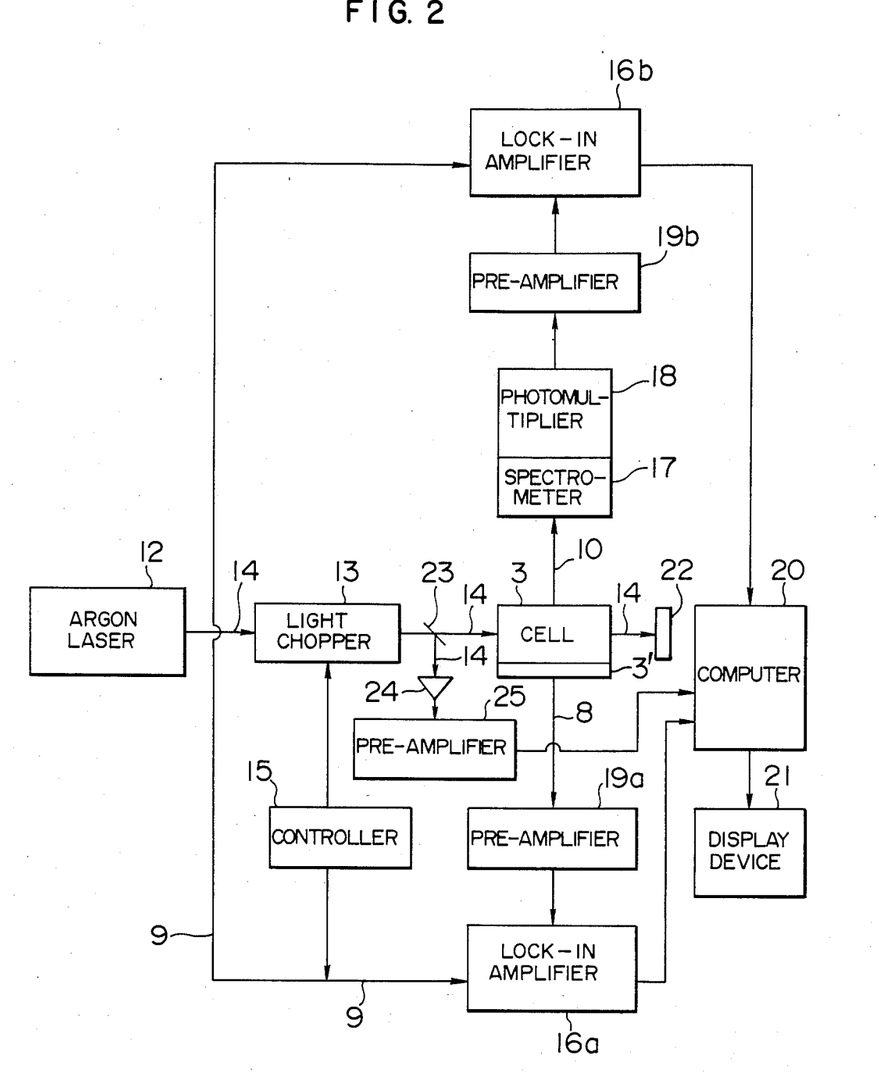
FIG. 2 is a block diagram showing an embodiment of an analyzer according to the present invention, which embodiment uses an argon laser as a light source.

FIG. 2 shows an embodiment of an analyzer according to the present invention which embodiment uses an argon laser as a beam source (namely, the electromagnetic wave generator), and measures a photoacoustic signal and fluorescence. Referring to FIG. 2, laser beam 14 emitted from an argon laser 12 is converted by a rotating-blade type light chopper 13 into intensity-modulated beam having a rectangular waveform. A modulating signal 9 supplied to the light chopper 13 is generated by a controller 15. The intensity-modulated beam 14 from the light chopper 13 is divided by a half mirror (namely, semitransparent mirror) 23 into two parts, one of which travels into a measuring cell 3 and the other impinges upon a photodetector 24. A photoacoustic signal which is generated within the cell by the intensity-modulated light 14, is detected by a piezoelectric element 3' and then amplified by a pre-amplifier 19a. The amplified photoacoustic signal is applied to a lock-in amplifier 16a, and thus only a photoacoustic signal component is selectively amplified. The lock-in amplifier 16a is the well-known amplifier for amplifying a weak signal separately from noise. The modulating signal 9 from the controller 15 is applied also to the lock-in amplifier 16a. The photoacoustic signal is modulated in accordance with the reference signal 9. Accordingly, when an output signal from the pre-amplifier 19a is amplified by the lock-in amplifier 16a in synchronism with the reference signal 9, the photoacoustic signal component can be amplified, selectively from the noise.

While, the spectrum of the light 10 is observed with a spectrometer 17 and a photomultiplier 18. An output signal from the photomultiplier 18 is very weak. Hence, like the photoacoustic signal detection, the above output signal is first amplified by a pre-amplifier 19b, and then only a signal component is amplified by a lock-in amplifier 16b. The output signals of the lock-in amplifiers 16a and 16b are applied to a computer 20, which calculates the constituent concentration of a solution having been introduced into the cell 3, from the intensities of the above output signals, and delivers the results of the calculation to a display device 21. The computer 20 may be an ordinary microcomputer capable of executing algorithms which will be mentioned later. The intensity-modulated beam 14 is detected by a photodetector, for example, a silicon photo-cell 24, and the output of the photo-cell 24 is applied to the computer 20 through a pre-amplifier 25, to normalize the photoacoustic signal magnitude and the fluorescence intensity. That is, the output signals of the lock-in amplifiers 16a and 16b are corrected by the output signal of the pre-amplifier 25, to obtain a constant analytical result independently of variations in output level of the argon laser 12. The laser beam 14 passed through the cell 3 is terminated by a stopper 22.

Figure 3:
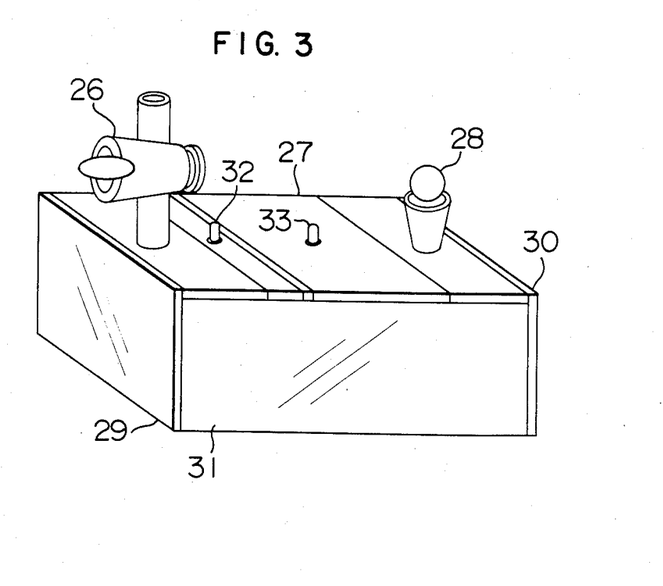
FIG. 3 is a perspective view showing a sample cell used in the embodiment of FIG. 2.

FIG. 3 shows the structure of the cell 3 used in the present embodiment. The cell having the form of a square box is filled with a solution which contains trace constituents to be determined. After a cock 26 has been turned on and a glass stopper 28 has been taken out, the solution is introduced into the cell. Of six side walls for forming the cell, three side walls are used as optical windows. The incident laser beam travels into the cell, along the center axis of the cell in the longitudinal direction thereof. An optical window 31 which forms one side wall of the cell, transmits the fluorescence generated in the solution. The cell is disposed so that the entrance slit (not shown) of the spectrometer 17 and the optical window 31 face each other. A piezoelectric element 27 is mounted on that side wall of the cell which is perpendicular to the optical window 31 and an optical window 29 receiving the incident laser beam. A photoacoustic signal generated in the solution is converted by the piezoelectric element 27 into an electric signal, and the potential difference between a positive electrode 32 and a negative electrode 33 is detected as the intensity of the above electric signal.

Figure 4:
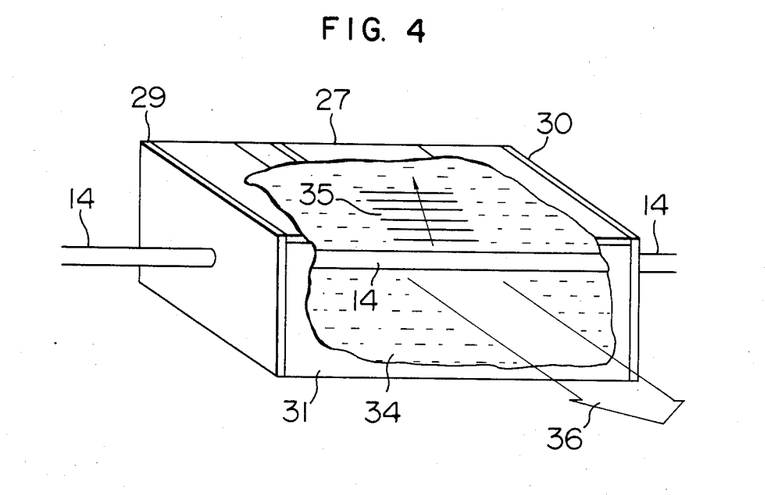
FIG. 4 is a partially cutaway view of the sample cell of FIG. 3.

FIG. 4 is a partially cutaway view of the cell of FIG. 3, and schematically shows the photoacoustic signal and the fluorescence which are generated within the cell.

Referring to FIG. 4, when the intensity-modulated laser beam 14 travels into the cell along the center axis thereof, a photoacoustic signal 35 and fluorescence 36 are simultaneously generated within a solution 34. As mentioned above, the photoacoustic signal is detected by the piezoelectric element 27, and the fluorescence passes through the optical window 31 and then impinges upon the spectrometer 17 of FIG. 2. The intensities of spectral components separated by the spectrometer 17 are detected by the photomultiplier 18.

Next, explanation will be made of a case where the concentrations of sexivalent uranium U(VI) and quadrivalent uranium U(IV) contained in a nitric acid solution are determined by the present embodiment, by way of example. It is impossible to discriminate a photoacoustic signal due to U(VI) from a photoacoustic signal due to U(IV) only by the photoacoustic analysis, but the resultant concentration of U(VI) and U(IV) can be determined at high sensitivity and with high accuracy by the photoacoustic analysis. While, U(VI) ions are high in fluorescent yield, but U(IV) ions are low in fluorescent yield and can scarcely generate fluorescence. Accordingly, only uranium U(VI) can be determined at high sensitivity by the fluorometric analysis. In the above case, respective concentrations of U(VI) and U(IV) are determined by utilizing the above-mentioned properties of U(VI) and U(IV). When the measured magnitude of photoacoustic signal, the measured intensity of fluorescence, the magnitude of photoacoustic signal caused by U(VI), the magnitude of photoacoustic signal caused by U(IV), the U(VI) concentration, and the U(IV) concentration are expressed by S, F, $S_{U6}$, $S_{U4}$, [U(VI)], and [U(IV)], respectively, we can obtain the following equations:

$$S = S_{U6} + S_{U4} \quad (2)$$

$$F = k'_{U6} [U(VI)] \quad (3)$$

$$S_{U6} = k_{U6} [U(VI)] \quad (4)$$

$$S_{U4} = k_{U4} [U(IV)] \quad (5)$$

where $k_{U6}$, $k_{U4}$, $k'_{U6}$ are proportional constants.

From the equations (2) to (5), we can obtain the following equations:

$$[U(VI)] = \frac{1}{k'_{U6}} F \quad (6)$$

$$[U(IV)] = \frac{1}{k_{U4}} \left( S - \frac{k_{U6}}{k'_{U6}} F \right) \quad (7)$$

That is, the U(VI) concentration is determined by the intensity F of fluorescence, and the U(IV) concentration is determined by the magnitude S of photoacoustic signal and the intensity F of fluorescence. Each of the proportional constants $k_{U4}$, $k_{U6}$ and $k'_{U6}$ is previously calculated from calibration curves which have been formed on the basis of measurement, and is previously stored in the computer 20. The calibration curves can be obtained by measuring the photoacoustic signal or fluorescence of each of solutions which contain a to-be-determined constituent at known concentrations. Actual procedure for determination the U(VI) concentration and the U(IV) will be explained below.

Figure 5:
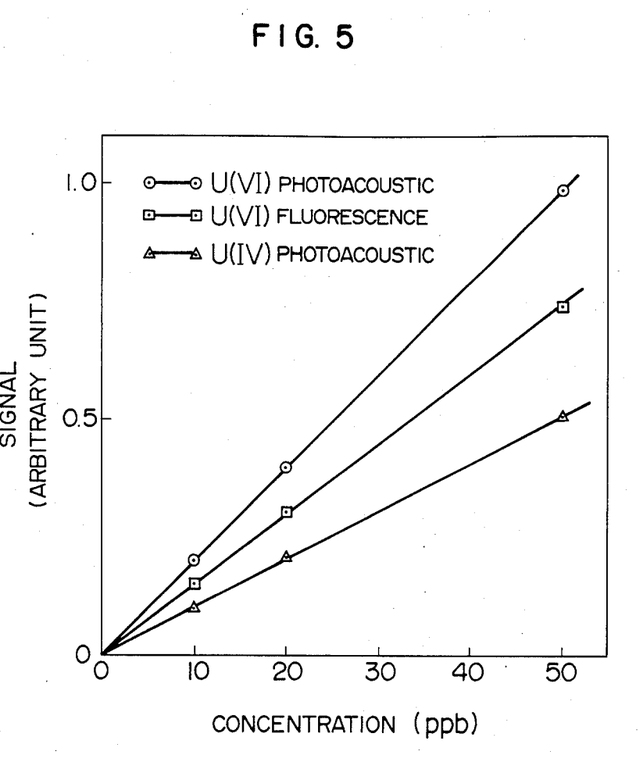
FIG. 5 is a graph showing examples of calibration curves of U(VI) and U(IV).

First, an argon laser 12 having lasing lines in a range from 350 to 370 nm and an output power of 1.3W is used as the beam source, the modulating frequency at the modulator 13 is set to 181 Hz, and the spectrometer 17 is set so that the fluorescence having a wavelength of 415 nm can be detected. Calibration curves of U(VI) and U(IV) are formed by using the present embodiment which is put in the above operating state. In more detail, three nitric acid solution containing sexivalent uranium U(VI) at concentrations of 10, 20 and 50 ppb are prepared, and a photoacoustic signal and fluorescence are measured by each of the above solutions to obtain the calibration curves of U(VI). Further, nitric acid solutions containing quadrivalent uranium U(IV) at concentrations of 10, 20 and 50 ppb are prepared, and a photoacoustic signal is measured for each of the solutions to obtain a calibration curve of U(IV). The calibration curves thus obtained are shown in FIG. 5. The proportional constants $k_{U6}$, $k'_{U6}$ and $k_{U4}$ are indicated by the slopes of the calibration curves of FIG. 5, and are given as follows:

$$k_{U4} = 0.01 \ (1/\text{ppb})$$

$$k_{U6} = 0.02 \ (1/\text{ppb})$$

$$k'_{U6} = 0.015 \ (1/\text{ppb})$$

Substitution of these values into the equations (6) and (7) gives the following equations:

$$[U(VI)] = 66.7 F \ (\text{ppb}) \quad (8)$$

$$[U(IV)] = 100 \ \{S - 1.3F\} \ (\text{ppb}) \quad (9)$$

Next, a nitric acid solution containing unknown amounts of U(VI) and U(IV) is analyzed by the present embodiment. That is, the cell is filled with the above solution, and a photoacoustic signal and fluorescence are simultaneously measured. In this case, it is known by measurement that the magnitude S of photoacoustic signal is equal to 0.8 and the intensity F of fluorescence is equal to 0.3. Using the equations (8) and (9), the computer 20 calculates the U(VI) concentration and U(IV) concentration as follows:

$$[U(VI)] = 20.0 \text{ ppb}, \ [U(IV)] = 41.0 \text{ ppb}$$

As mentioned above, according to the present embodiment, it is possible to determine the U(IV) concentration which cannot be detected by a conventional apparatus for fluorometric analysis, and to determine respective concentrations of U(IV) and U(VI) which cannot be separated from each other by a conventional apparatus for photoacoustic analysis.

Further, when the intensity of the excitation beam used in the present invention is made large enough to put constituents contained in a solution, into a plasma state, the constituents can generate not only fluorescence and phosphorescence but also plasma emission. Unlike the fluorescence and phosphorescence, the plasma emission can be generated by almost all substances. At the same time as plasma emission is generated by a substance, a photoacoustic signal is generated which has a magnitude proportional to the concentration of the substance. Accordingly, almost all substances can be identified and the concentration of each of the substances can be determined, by measuring an emission spectrum, the intensity of radiation and the magnitude of photoacoustic signal, at the same time.

Figure 6:
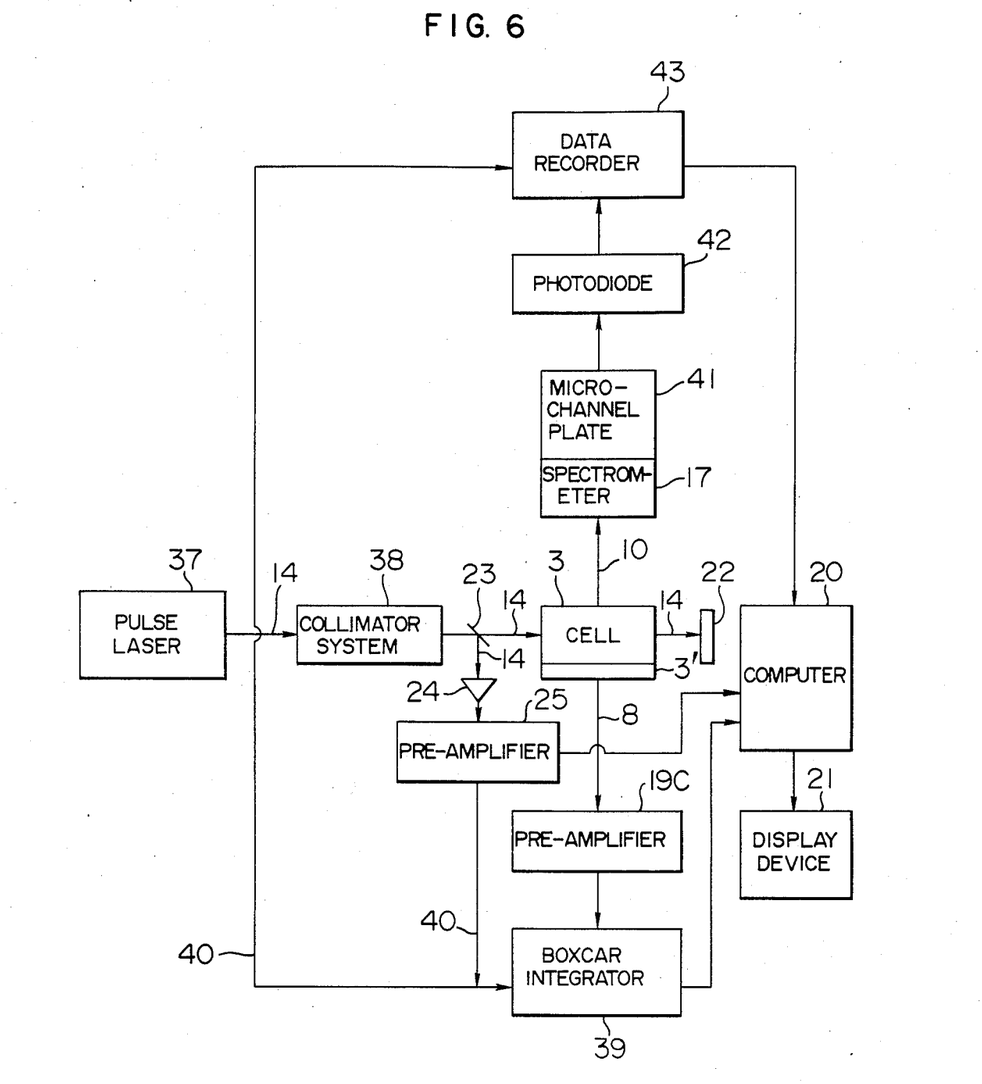
FIG. 6 is a block diagram showing another embodiment of an analyzer according to the present invention, which embodiment utilizes plasma emission.

FIG. 6 shows another embodiment of an analyzer according to the present invention, in which embodiment plasma emission is generated. Referring to FIG. 6, a pulse laser 37 is used as the light source to increase the energy density of the excitation beam, and the plasma emission is detected by the combination of a microchannel plate 41 and a photodiode 42 in order to be able to detect a desired spectral component of the plasma emission when a solution in the cell 3 is irradiated with a single light pulse. Further, in the present embodiment, the photoacoustic signal is a single pulse signal. Accordingly, the waveform of the photoacoustic signal is obtained by a boxcar integrator 39, and the signal magnitude is applied the computer 20. The present embodiment performs substantially the same operation as the embodiment of FIG. 2. The boxcar integrator 39 is a well-known apparatus for obtaining a weak signal form having an extremely short duration time from noise field. An output signal from a pre-amplifier 19C is applied to the boxcar integrator 39 in synchronism with a pulse signal which is outputted from a pre-amplifier 25 and corresponds to the laser light pulse. The microchannel plate 41 is formed of a multiplicity of fine light-detecting elements which are arranged in the form of an array, and measures a spectrum of the radiation obtained by the spectrometer 17, at a time. The photodiode 42 detects a signal from the micro-channel plate 41, and the output of the photodiode 42 is recorded in a data recorder 43 in synchronism with the pulse signal from the pre-amplifier 25, that is, the laser light pulse from the pulse laser 37. Other parts than the above-mentioned perform the same operation as those of the embodiment of FIG. 2, and hence explanation of such parts will be omitted for the sake of simplicity.

In the present invention, X-rays, γ-rays or infrared rays can be applied for the electromagnetic wave source instead of the laser beam to obtain the same effect as of the embodiments that have been specifically described.

We claim:

1. A method of simultaneous determination of trace constituents, comprising the steps of:
    irradiating a solution containing trace constituents with an intensity-modulated electromagnetic wave having a predetermined wavelength;
    detecting the magnitude of a photoacoustic signal generated by said trace constituents which have been irradiated with the intensity-modulated electromagnetic wave;
    detecting the intensity of light radiation from said trace constituents which have been irradiated with the intensity-modulated electromagnetic wave, and detecting the emission spectrum of said electromagnetic-wave irradiated trace constituents; and
    calculating the concentrations of said trace constituents from the detected magnitude of said photoacoustic signal, the detected intensity of said light radiation, and calibration curves each formed for known concentrations of one of said trace constituents, and identifying said trace constituents by the detected emission spectrum, and wherein
    said step of calculating the concentrations of said trace constituents includes a step of determination of said trace constituents by solving simultaneous equations with variables of the magnitude of photoacoustic signal and the intensity of emitted light with respect to concentration of each trace constituent.

2. A method of simultaneous determination of trace constituents as claimed in claim 1, wherein said intensity-modulated electromagnetic wave is a light pulse having said predetermined wavelength.

3. A method of simultaneous determination of trace constituents as claimed in claim 2, wherein said light pulse is a laser pulse.

4. A method of simultaneous determination of trace constituents as claimed in claim 1, wherein said intensity-modulated electromagnetic wave is an infrared radiation.

5. A method of simultaneous determination of trace constituents as claimed in claim 1, wherein said intensity-modulated electromagnetic wave is an infrared radiation.

6. A method of simultaneous determination of trace elements as claimed in claim 1, wherein the waveform of a modulating signal for producing said intensity-modulated electromagnetic wave is one of a rectangular waveform and a sinusoidal waveform.

7. A method of simultaneous determination of trace constituents as claimed in claim 1, wherein said radiation from said trace constituents is one to fluorescence and phosphorescence.

8. A method of simultaneous determination of trace constituents as claimed in claim 1, wherein the step of identifying said trace constituents involves a substantially simultaneous processing of the photoacoustic signal and the detected intensity of the light radiation.

9. An apparatus for simultaneous determination of trace constituents, comprising:
    a cell including means for holding a solution therein, said solution containing trace constituents;
    optical means for generating an intensity-modulated electromagnetic wave having a predetermined wavelength to irradiate said cell with the intensity-modulated electromagnetic wave;
    first detection means for detecting the photoacoustic signal generated by said trace constituents which have been irradiated with the intensity-modulated electromagnetic wave;
    second detection means for detecting the intensity of light radiation from said trace constituents which have been irradiated with said intensity-modulated electromagnetic wave, and for detecting the emission spectrum of said electromagnetic-wave irradiated trace components;
    means for calculating the concentrations of said trace constituents from the detected magnitude of said photoacoustic signal, the detected intensity of said light radiation, and calibration curves each formed for know concentrations of one of said trace constituents; and
    means for identifying said trace constituents by the detected emission spectrum;
    wherein said means for calculating the concentrations of said trace constituents includes means for solving simultaneous equations which contain the magnitude of photoacoustic signal and the intensity of emitted radiation for concentration of each trace constituent.

10. An apparatus according to claim 9, wherein said intensity-modulated electromagnetic wave is a light pulse.

11. An apparatus according to claim 9, wherein said light pulse is a laser pulse.

12. An apparatus according to claim 9, wherein said intensity-modulated electromagnetic wave is infrared radiation .

13. An apparatus according to claim 9, wherein the waveform of a modulating signal for producing said intensity-modulated electromagnetic wave is one of a rectangular waveform and a sinusoidal waveform.

14. An apparatus according to claim 9, wherein means for identifying said trace constituents includes signals that are received substantially simultaneously from said first and second detection means.

* * * * *